US00PP34281P2

(12) United States Plant Patent
Van Swieten

(10) Patent No.: US PP34,281 P2
(45) Date of Patent: May 31, 2022

(54) ***PHALAENOPSIS* ORCHID PLANT NAMED 'PHA217131'**

(50) Latin Name: ***Phalaenopsis* hybrid**
Varietal Denomination: PHA217131

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,028

(22) Filed: Jan. 13, 2022

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHA217131', particularly characterized by having dark reddish-purple flowers with small light reddish-purple centers and dark red lips, flowers that are concave in lateral view, apical lobes of the lip with a small bump and ridge, and is propagated by meristem tissue culture, is disclosed.

3 Drawing Sheets

Genus and species: *Phalaenopsis* hybrid.
Variety denomination: 'PHA217131'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA217131'.

The new *Phalaenopsis* plant is a product of a planned breeding program conducted by the inventor in Bleiswijk, the Netherlands. The objective of this breeding program was to create a new *Phalaenopsis* plant with attractive, dark reddish-purple flowers with small light reddish-purple centers and dark red lips, suitable for potted plant production.

The new *Phalaenopsis* plant 'PHA217131' is a result of cross-pollination made by the inventor in January 2013 in Bleiswijk, the Netherlands, of the proprietary female, or seed parent, *Phalaenopsis* hybrid '17956-06' (unpatented) with the proprietary male, or pollen parent, *Phalaenopsis* hybrid '01-3389' (unpatented).

The new *Phalaenopsis* was selected by the inventor as a single plant within the progeny of the stated cross-pollination in a controlled greenhouse in Bleiswijk, the Netherlands, in November 2015. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 29, 2021 (Application no. 2021/0306), by Applicant who obtained the subject matter disclosed directly from the inventor. 'PHA217131' has not been made publicly available or sold anywhere in the world prior to the effective filing date of this application with the exception of sales or disclosures made one year or less before the effective filing date of this claimed invention by Applicant who obtained 'PHA217131' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA217131' as a new and distinct variety of *Phalaenopsis* plant:

1) Dark reddish-purple flowers with small light reddish-purple centers and dark red lips;
2) Flower shape in lateral view is concave; and
3) Apical lobe of the lip has a small bump and ridge.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in November 2021. Colors in the photographs may differ from the color values cited in the detailed botanical description, which accurately describe the actual colors of the new variety.

DESCRIPTION OF THE NEW VARIETY

Figure 1:
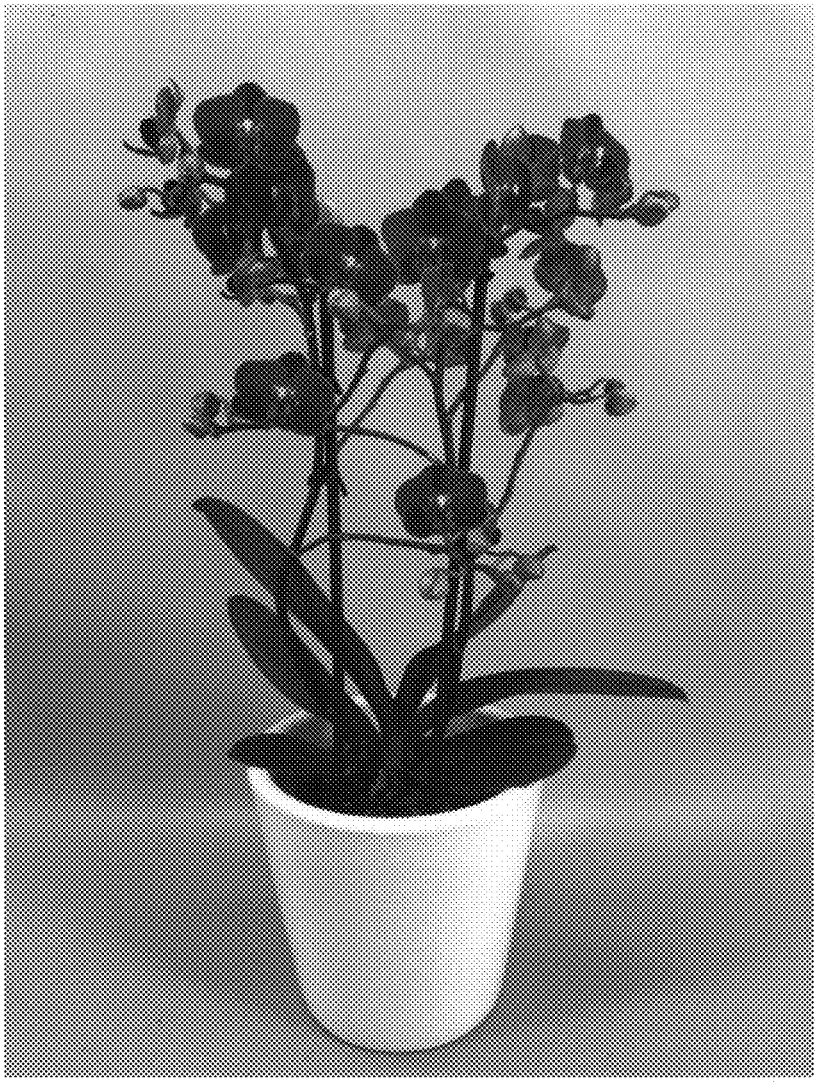
FIG. 1 shows the overall plant habit, including blooms, buds, and foliage of 'PHA217131'.
Figure 2:
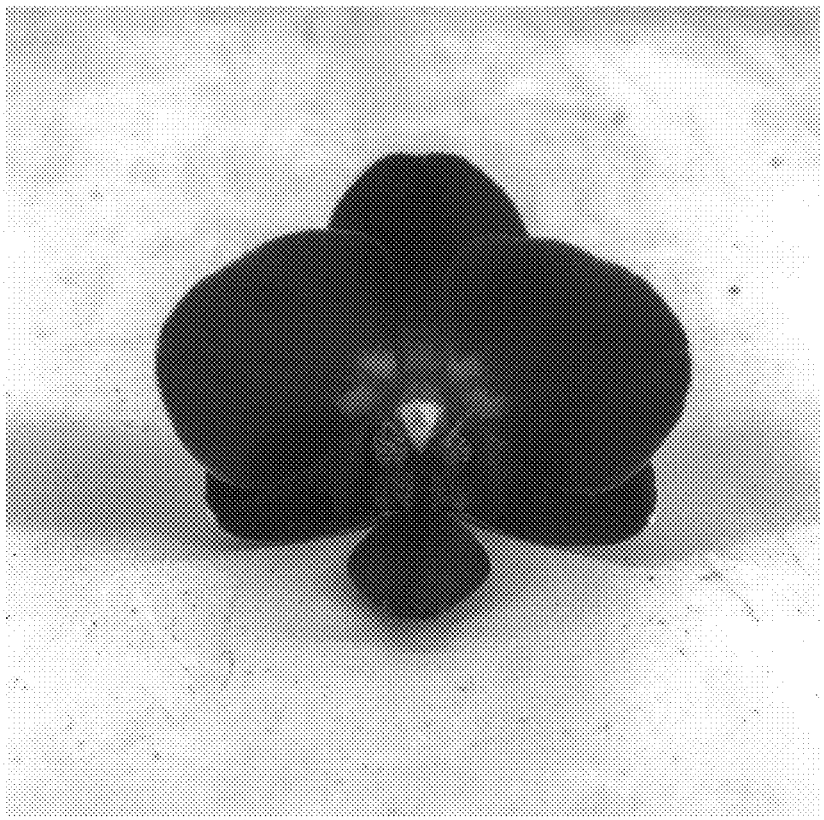
FIG. 2 shows a close-up of a flower of 'PHA217131'.
Figure 3:
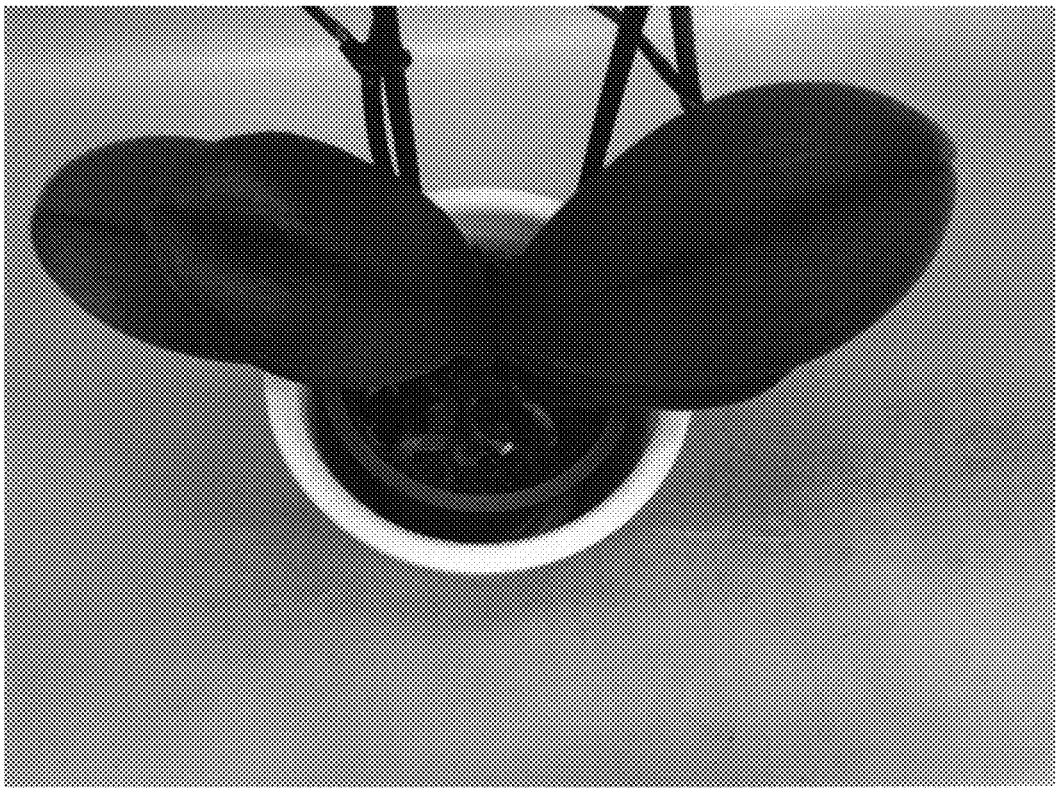
FIG. 3 shows an overhead view of the leaves of 'PHA217131'.

The following detailed description sets forth the distinctive characteristics of 'PHA217131'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA217131'.

Parentage:

*Female parent*.—*Phalaenopsis* cultivar '17956-06' (unpatented).

*Male parent*.—*Phalaenopsis* cultivar '01-3389' (unpatented).

Propagation:

*Type*.—Meristem tissue culture.

Roots:

*Root description*.—Greyed-green (a color in between RHS 190B and RHS 190C) colored roots with branching lateral roots having light yellow-green (RHS 145B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 30.0 cm to 35.0 cm.

*Width* (*measured from leaf tips*).—About 26.0 cm to 28.0 cm.

*Vigor*.—Strong.

Leaves:

*Mature leaves*.—Quantity per plant: 8 to 9 leaves are produced before flowering. Length (fully expanded): 13.0 cm to 15.0 cm. Width: 6.5 cm to 7.5 cm. Position of the broadest part of the leaf: At the middle. Shape: Oblong. Base shape: Slightly elongated. Apex: Obtuse asymmetric. Leaf blade angle with the petiole (measured from the horizontal position): Between 20 degrees and 40 degrees. Leaf margin: Entire. Color: Upper surface: RHS 147A. Lower surface: RHS 146B with a touch of brown (RHS 200B) at the margin. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146B.

Peduncle:

*Quantity per plant*.—2.

*Number of flowers per peduncle*.—26 to 30.

*Length*.—30.0 cm to 35.0 cm.

*Diameter*.—4.0 mm to 5.0 mm.

*Strength*.—Strong.

*Aspect*.—Upright to slightly pendent.

*Texture*.—Smooth.

*Color*.—Yellow-green (RHS 146B) with a touch of brown (RHS 200B).

*Internode length*.—1.5 cm to 2.5 cm

Inflorescence description:

*Appearance*.—Upright to slightly pendent, panicle inflorescence with bilaterally symmetrical flowers that open in succession beginning with the lowermost flower..

*Number of inflorescences*.—2.

*Inflorescence size*.—Height (from base to tip): 210.0 mm to 230.0 mm.

*Flowering time*.—First flowers can be expected 10 to 11 months after planting in a 12-cm pot.

*Flower*.—Height: 35.0 mm to 40.0 mm. Diameter: 40.0 mm to 45.0 mm. Depth of lip: 15.0 mm to 17.0 mm.

*Flower shape*.—Concave.

*Flower longevity*.—On the plant: 8 to 10 weeks.

*Fragrance*.—Absent.

*Flower bud*.—Average size: Medium. Length: 14.0 mm to 16.0 mm. Width: 13.0 mm to 15.0 mm. Shape: Egg shaped. Color: Yellow-green (RHS 146D) at the base and lighter yellow-green (RHS 145C) toward the tip with red-purple shade and stripes (a color in between RHS N77B and RHS N79D).

*Petals*.—Arrangement: Open/free. Shape: Semi-circular. Apex: Rounded asymmetric. Margin: Moderately undulated. Length (from base to tip): 18.0 mm to 20.0 mm. Width: 22.0 mm to 24.0 mm.. Position of the broadest part of the petal: Toward the base Color (when fully opened): Upper surface: Basic color: Dark reddish-purple (a color in between RHS N79C and RHS N78A). Over color: Light reddish-purple (RHS N78D) at the base. Lower surface: Basic color: Reddish-purple (RHS N78A). Over color: Light purple (RHS 76A) at the middle from the center toward tip. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 19.0 mm to 21.0 mm. Width: 17.0 mm to 19.0 mm. Position of the broadest part of the dorsal sepals: At the middle. Color (when fully opened): Upper surface: Basic color: Dark reddish-purple (a color in between RHS N79C and RHS N78A). Over color: Purplish-pink at the base and dots (RHS N78C). Lower surface: Basic color: Reddish-purple (RHS N79D). Over color: Light yellow-green (RHS 195B) and touch of light reddish-purple (RHS N78D). Number of spots, dots, and stripes on the dorsal sepals (upper surface): Few small dots. Color of spots, dots, and stripes on the dorsal sepals (upper surface): RHS N78C. Density of netting of the dorsal sepals (upper surface): None. Color of the netting (upper surface): Not applicable.

*Lateral sepals*.—Shape: Ovate. Apex: Obtuse asymmetric. Margin: Entire. Length (from base to tip): 18.0 mm to 20.0 mm. Width: 15.0 mm to 17.0 mm. Position of the broadest part of the lateral sepals: Toward the base. Color (when fully opened): Upper surface: Basic color: Dark reddish-purple (RHS N79C). Over color: Touch of light yellow (RHS 145D) with dark purplish-red dots (RHS N79C) at the base; dark red shade (RHS 187B). Lower surface: Basic color: Reddish-purple (RHS N79D). Over color: Light yellow-green (RHS 145C). Number of spots, dots, and stripes on the lateral sepals (upper surface): Medium of very small dots. Color of spots, dots, and stripes on the lateral sepals (upper surface): RHS N79C. Density of netting of the lateral sepals (upper surface): None. Color of the netting (upper surface): Not applicable.

*Labellum* (*lip*).—Whiskers: Present, but very short. Length of whiskers: 1.0 mm to 2.0 mm.. Color of whiskers: Dark red-purple (a color in between RHS 187B and RHS N79B) Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 12.0 mm to 14.0 mm. Width: 7.0 mm to 9.0 mm. Color: Upper surface: Touch of yellow (RHS 13B) at the base; dotted (RHS 183A); dark red (a color in between RHS 187A and RHS 187B) toward the tip. Lower surface: Very light purple (RHS 76D) at the base; reddish-purple (RHS N78A) and dark red-purple (a color in between RHS 187B and RHS N79B) toward margins. Number of spots, dots, and stripes on the lateral lobe: Few dots at the base. Color of spots, dots, and stripes on the lateral lobe: RHS 183A. Density of netting of the lateral lobe: None. Color of the netting: Not applicable.

*Apical lobe*.—Shape: Elliptic. Margin: Entire. Length: 14.0 mm to 16.0 mm. Width: 11.0 mm to 13.0 mm. Color: Upper surface: Touch of yellow (RHS 11C) at the base; dark red (RHS 187B) with a touch of RHS N79B toward whiskers. Lower surface: Dark red wings (RHS 187B); dark purplish-red (RHS N79C) toward the middle and light yellow-green (RHS 157B) at the middle from the base toward the tip. Number of spots and stripes on the apical lobe: None. Color of spots and stripes on the apical lobe: None. Density of netting of the apical lobe: None. Color of the netting: None. Bump and ridge: Present (small).

*Callus*.—Average size: Small. Height: 4.0 mm to 5 0 mm. Length: 4.0 mm to 5.0 mm. Width: 3.0 mm to 4.0 mm. Color: Yellow tips (RHS 13A); dotted (RHS 59B); light yellow (RHS 11C) on sides.

Reproductive organs:

*Column*.—Length: 6.0 mm to 7.0 mm. Diameter: 3.0 mm to 4.0 mm. Color: Reddish-purple (RHS N78A).

*Pollinia*.—Quantity: 2. Diameter: 0.7 mm to 0.8 mm. Color: Orange-yellow (RHS 23A).

*Ovary*.—Length: 7.0 mm to 9.0 mm. Diameter: 1.8 mm to 2.0 mm.

*Pedicel*.—Length: 25.0 mm to 27.0 mm. Diameter: 2.1 mm to 2.3 mm. Color: Yellow-green (a color in between RHS 144B and RHS 144C) at the base; light yellow-green (RHS 145C) and light purple (RHS 76A) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA217131' differs from the female parent plant '17956-06' (unpatented) in that 'PHA217131' has elliptic apical lobes and leaves with no anthocyanin coloration on the upper surface, whereas '17956-06' has rhombic apical lobes and leaves with very weak to weak anthocyanin coloration on the upper surface. Additionally, 'PHA217131' has smaller flowers than '17956-06'.

'PHA217131' differs from the male parent plant '01-3389' (unpatented) in that 'PHA217131' has pedicels with a main color of yellow-green and elliptic apical lobes, whereas '01-3389' has pedicels with a main color of light reddish-purple and ovate apical lobes.

'PHA217131' is most similar to the commercial *Phalaenopsis* plants named 'PHALFEMYM' (U.S. Plant Pat. No. 29,783) and 'PHALBIRWIN' (U.S. Plant Pat. No. 33,727). 'PHA217131' differs from the commercial variety 'PHALFEMYM' in that 'PHA217131' has elliptic apical lobes, dark red-purple whiskers, and leaves with a semi-erect attitude, whereas 'PHALFEMYM' has ovate apical lobes, red-purple whiskers, and leaves with a horizontal to semi-drooping attitude.

'PHA217131' differs from the commercial variety 'PHALBIRWIN' in that 'PHA217131' has elliptic apical lobes, dark red-purple whiskers, and flowers that are concave in lateral view, whereas 'PHALBIRWIN' has circular apical lobes, dark purplish-red whiskers with small white tips, and flowers that are flat in lateral view.

I claim:

1. A new and distinct variety of *Phalaenopsis* plant named 'PHA217131', substantially as described and illustrated herein.

* * * * *